(12) United States Patent
Lloyd et al.

(10) Patent No.: US 11,016,073 B2
(45) Date of Patent: *May 25, 2021

(54) APPARATUS, SYSTEM, AND METHOD FOR WATER CONTAMINANT TESTING

(71) Applicant: Field Water Testing, LLC, Bountiful, UT (US)

(72) Inventors: Christopher Lloyd, West Valley City, UT (US); Andrew Duncan, Logan, UT (US)

(73) Assignee: Field Water Testing, LLC, Bountiful, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/534,991

(22) Filed: Aug. 7, 2019

(65) Prior Publication Data

US 2019/0360989 A1 Nov. 28, 2019

Related U.S. Application Data

(63) Continuation of application No. 15/227,866, filed on Aug. 3, 2016, now Pat. No. 10,422,782.
(Continued)

(51) Int. Cl.
*G01N 33/18* (2006.01)
*G01N 21/78* (2006.01)
(Continued)

(52) U.S. Cl.
CPC ......... *G01N 33/1826* (2013.01); *G01N 21/59* (2013.01); *G01N 21/643* (2013.01);
(Continued)

(58) Field of Classification Search
CPC .. G01N 33/1826; G01N 33/18; G01N 21/643; G01N 21/78; G01N 21/6428;
(Continued)

(56) References Cited

U.S. PATENT DOCUMENTS

| 5,552,297 A | 9/1996 | Wong et al. |
| 5,731,212 A | 3/1998 | Gavin et al. |

(Continued)

FOREIGN PATENT DOCUMENTS

| JP | 02-010136 A | 1/1990 |
| JP | 2000-510592 A | 8/2000 |

(Continued)

OTHER PUBLICATIONS

PCT/US2016/045420, Notification of Transmittal of the International Search Report and the Written Opinion of the International Searching Authority, or the Declaration, dated Oct. 17, 2016, 12 pages.

*Primary Examiner* — Christine T Mui
(74) *Attorney, Agent, or Firm* — Kunzler Bean & Adamson

(57) ABSTRACT

A system, device, and method for detecting and quantifying an analyte in a liquid include a vial having one or more pre-dosed reagents disposed in the vial. The vial is configured to hold a volume of a liquid including an analyte. The one or more pre-dosed reagents are dissolvable in the volume of the liquid to form a sample liquid solution comprising chromophores or fluorophores. The analyte and the one or more pre-dosed reagents react to yield the chromophores or fluorophores. The system further includes a detection device including a chamber configured to retain the vial, the detection device configured to quantify the analyte in the sample liquid solution. A device and method may perform the functions of the system.

19 Claims, 8 Drawing Sheets

Related U.S. Application Data

(60) Provisional application No. 62/200,484, filed on Aug. 3, 2015.

(51) Int. Cl.
*G01N 21/59* (2006.01)
*G01N 21/64* (2006.01)
*G01N 21/80* (2006.01)
*G01N 21/77* (2006.01)

(52) U.S. Cl.
CPC .............. *G01N 21/78* (2013.01); *G01N 21/80* (2013.01); *G01N 2021/7786* (2013.01); *G01N 2201/0691* (2013.01)

(58) Field of Classification Search
CPC ........ G01N 21/63; G01N 21/77; G01N 21/75; G01N 21/59
USPC .......... 422/401, 82.08, 400, 50, 82.01, 68.1; 436/130
See application file for complete search history.

(56) References Cited

U.S. PATENT DOCUMENTS

| | | |
|---|---|---|
| 7,652,267 B2 | 1/2010 | Tokhtuev et al. |
| 2002/0001539 A1 | 1/2002 | DiCesare et al. |
| 2003/0058450 A1 | 3/2003 | Mosley et al. |
| 2005/0112023 A1 | 5/2005 | Liang |
| 2008/0166792 A1 | 7/2008 | Attar et al. |
| 2012/0015449 A1* | 1/2012 | Fiedler ................ G01N 33/146 436/501 |
| 2012/0045826 A1* | 2/2012 | Yantz ................ A61B 5/15186 435/288.7 |
| 2013/0330245 A1 | 12/2013 | Duncan et al. |
| 2014/0070078 A1 | 3/2014 | Land et al. |

FOREIGN PATENT DOCUMENTS

| | | |
|---|---|---|
| JP | 2005-536713 A | 12/2005 |
| WO | 98/38493 A1 | 9/1998 |
| WO | 03/040702 A1 | 5/2003 |
| WO | 2012/088054 A1 | 6/2012 |
| WO | 2015098967 A1 | 7/2015 |

\* cited by examiner

APPARATUS, SYSTEM, AND METHOD FOR WATER CONTAMINANT TESTING

CROSS-REFERENCE TO RELATED APPLICATIONS

This application is a continuation of U.S. Pat. No. 10,422,782, filed Aug. 3, 2016, which claims the benefit of U.S. Provisional Application No. 62/200,484, filed Aug. 3, 2015, each of which is hereby incorporated by reference herein in its entirety, but not limited to those portions that specifically appear hereinafter, the incorporation by reference being made with the following exception: In the event that any portion of the above-referenced provisional application is inconsistent with this application, this application supersedes said above-referenced provisional application.

BACKGROUND

The detection of analytes in a liquid (e.g., contaminants in wastewater) has numerous useful applications. For example, contaminant monitoring in manufacturing is important when water quality has a direct impact on materials manufactured and when water discharges are monitored for permit compliance. In agriculture, water that was previously directed to disposal by injection could be easily monitored for suitability for crop irrigation. With the ability to quickly detect and monitor major macro and micro minerals of dietary importance, Concentrated Animal Feeding Operations ("CAFO") programs could be closely monitored to ensure optimum production with minimal waste. Water and wastewater management are also important for industries and regulatory bodies involved in energy production and extraction.

Additionally, the revolution in hydraulic fracturing and horizontal drilling methods has made formerly inaccessible oil and gas commercially profitable. These methods depend on the use and management of large quantities of water. The ability to quickly and accurately determine water quality is crucial to modern drilling, fracturing, and oilfield processing of waste streams. Specifically, constituents in water need to be determined for the following reasons:

1. Baseline water quality within the natural aquifers surrounding the potential drilling area needs to be determined before any drilling activity takes place and monitored throughout the drilling and production process to ensure no cross-contamination of water resources has occurred.

2. Metals (and other inorganic ions) and organic constituents must be compatible with drilling mud chemistries to optimize drilling schedules, reduce maintenance or equipment costs and meet environmental standards while drilling through aquifers.

3. Salt, metal ions, anions (especially borates) and organics must be monitored to optimize gel chemistries for fracturing operations. (Bad fracturing stages caused by unmanaged water quality can cost millions of dollars over the life of a well.)

4. Depending on the geological formation, one recovers between 3 to 11 barrels of water for each barrel of oil—this wastewater must be properly collected, stored and disposed of or optimally reused. The accurate determination of normally encountered metals, anions, microbes and organic constituents (usually coming up from the geological formation) is critical for mixing waste streams, reducing maintenance due to scaling and preventing corrosion of oilfield production and waste storage and transportation assets.

5. Monitoring water constituents is critical for EOR (enhanced oilfield recovery) to maximize hydrocarbon recovery and to prevent damage to the formation (especially when produced and flowback wastewaters are utilized).

Critical water monitoring is usually accomplished through a mixture of certified laboratory testing (for initial oilfield chemical development and environmental certifications) and on-site testing for operations and wastewater management. On-site chemical testing in the oilfield usually relies on kits and instruments that were originally developed for municipal and well water applications and suffer from the following issues:

1. Most kits suffer from a limited dynamic range requiring time-consuming dilutions and the resulting reduction in precision.

2. Many kits are titrimetric and require varying degrees of training and experience to produce reliable results. (Even after one develops the skills to conduct the assay the tests suffer from accuracy issues due to variability caused by the drop counting methods employed.)

3. During the time required for accurate off-site testing, cross contamination may substantially impact the freshwater sources.

4. Chemical testing kits also consume a considerable amount of time—dilutions, conducting the tests and clean up between assays often consume critical time (especially during fracturing operations when analysis speed can prevent failed fracturing stages).

5. Methods that were developed for drinking water aquifers can suffer from interferences that are present in oilfield waters (resulting in lost revenue and problems from poor fracturing stages and plugging of formations and oilfield assets due to inaccurate or absent water testing results). Methods that were developed for monitoring pH suffer from issues that make them inaccurate when conductivities are extremely low or moderately high.

6. Chemical testing kits that use instruments require specialized training and time-consuming reagent handling and calibration steps for proper function.

Rapid, sensitive and on-site water monitoring is also critical for ensuring that wastewater discharge meets contractual or environmental limits for agricultural, municipal and industrial runoff requirements as well as a critical step in wastewater management.

SUMMARY

The subject matter of the present application has been developed in response to the present state of the art, and in particular, in response to the shortcomings of testing liquids to quantify an analyte, that have not yet been fully solved by currently available techniques.

According to one embodiment, a system for detecting and quantifying an analyte in a liquid includes a vial including one or more pre-dosed reagents disposed in the vial. The vial is configured to hold a volume of a liquid including an analyte. The one or more pre-dosed reagents are dissolvable in the volume of the liquid to form a sample liquid solution comprising chromophores or fluorophores. The analyte and the one or more pre-dosed reagents react to yield the chromophores or fluorophores. The system further includes a detection device including a chamber configured to retain the vial, the detection device configured to quantify the analyte in the sample liquid solution.

According to one embodiment, the pre-dosed reagents include freeze-dried solid reagents. In certain implementations, quantifying the analyte includes quantifying the chromophores or fluorophores in the sample liquid solution.

According to one embodiment, the detection device includes a plurality of light sources, each light source configured to emanate light towards the sample liquid solution in the vial.

In some implementations, the detection device includes a first photosensitive detector positioned in the chamber opposite from at least one of the plurality of light sources. According to one embodiment, the first photosensitive detector detects transmission of light through the sample liquid solution.

According to some implementations, the detection device includes a second photosensitive detector positioned at an angle offset from direct light from a plurality of light sources. According to one embodiment, the second photosensitive detector detects fluorescence of light from the sample liquid solution.

In some implementations, the plurality of light sources are each modulated at a fixed frequency.

According to one embodiment, the first photosensitive detector includes a photosensor configured to convert a light signal from the plurality of light sources to a voltage signal, an amplifier configured to amplify the voltage signal, and a demodulator configured to convert the voltage signal to a direct current signal.

According to some implementations, the detection device further includes a control system including an analog to digital converter to measure the direct current signal.

In some implementations, the detection device is configured to detect light signals that pass through the sample liquid solution and convert the detected light signals into digital signals to quantify the chromophores or fluorophores in the sample liquid solution.

According to one embodiment, a detection device for detecting and quantifying an analyte in a liquid includes a chamber configured to receive and retain a vial including one or more pre-dosed reagents disposed within the vial. The vial is configured to receive and hold a volume of a liquid including an analyte and the one or more pre-dosed reagents are dissolvable in the volume of the liquid to form a sample liquid solution including chromophores or fluorophores. The analyte and the one or more pre-dosed reagents react to yield the chromophores or fluorophores. The device includes a plurality of light sources, each light source configured to emanate light towards the sample liquid solution in the vial, a first photosensitive detector positioned in the chamber opposite from at least one of the plurality of light sources, and second photosensitive detector positioned at an angle offset from direct light from plurality of light sources.

In some implementations, the first photosensitive detector includes a photosensor configured to convert a light signal from the plurality of light sources to a voltage signal, an amplifier configured to amplify the voltage signal, and a demodulator configured to convert the voltage signal to a direct current signal.

According to one embodiment, a method for detecting and quantifying an analyte in a liquid includes forming a sample liquid solution by inserting a volume of a liquid including an analyte into a vial with one or more pre-dosed reagents dissolvable in the volume of the liquid to form a sample liquid solution including chromophores or fluorophores. The analyte and the one or more pre-dosed reagents react to yield the chromophores or fluorophores. The method includes quantifying the analyte in the sample liquid solution by quantifying the chromophores or fluorophores in the sample liquid solution.

In some implementations, quantifying the chromophores or fluorophores in the sample liquid solution includes detecting light transmission through the sample liquid solution using a first photosensitive detector positioned opposite a plurality of light sources and detecting light fluorescence from the sample liquid solution using a second photosensitive detector positioned offset from direct light emanation from the plurality of light sources.

According to one embodiment, the method includes modulating the light sources at a fixed frequency.

According to some embodiments, the method includes converting the detected light transmission to an electrical signal. In some implementations, converting the detected light transmission to an electrical signal includes converting the detected light transmission to a voltage signal, amplifying the voltage signal, and converting the amplified voltage signal to a direct current signal.

According to some embodiments, quantifying the analyte in the sample liquid solution includes detecting absorbance in the sample liquid solution.

The described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims or may be learned by the practice of the subject matter as set forth hereinafter.

BRIEF DESCRIPTION OF THE DRAWINGS

In order that the advantages of the subject matter of the present disclosure will be readily understood, a more particular description of the subject matter will be rendered by reference to specific embodiments that are illustrated in the appended drawings. Understanding that these drawings depict only typical embodiments of the subject matter of the present disclosure and are not, therefore, to be considered to be limiting of its scope, the subject matter will be described and explained with additional specificity and detail through the use of the accompanying drawings, in which.

DETAILED DESCRIPTION

Figure 1:
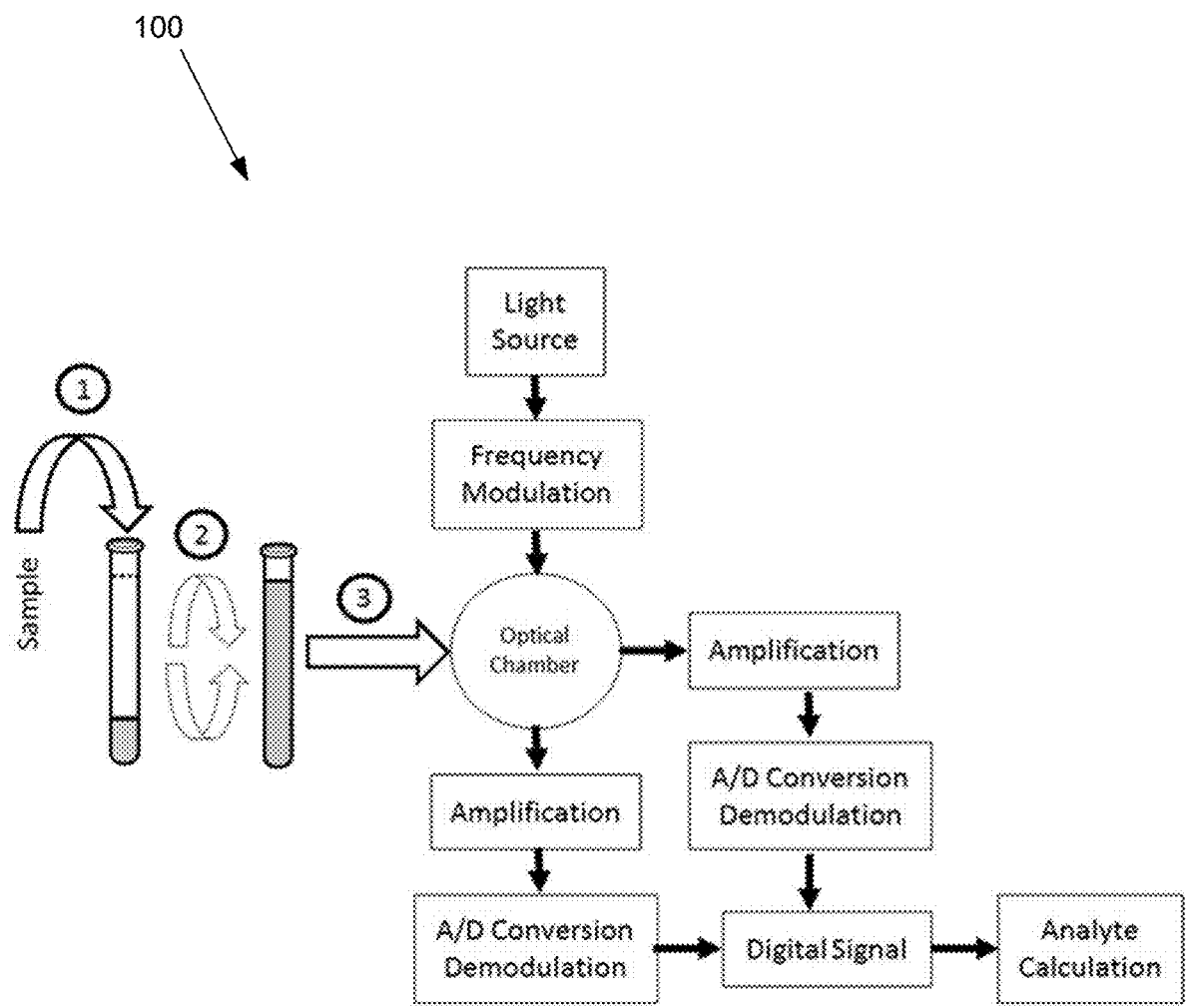
FIG. 1 is a schematic flow chart diagram of a method for testing water, according to one embodiment.

The subject matter of the present disclosure has been developed in response to the present state of the art in water and other fluid testing procedures. Accordingly, the subject matter of the present disclosure has been developed to provide an apparatus, system, and method for testing water and other liquids for contaminants that overcomes many or all or some shortcomings in the prior art.

Reference throughout this specification to features, advantages, or similar language does not imply that all of the features and advantages that may be realized with the subject matter of the present disclosure should be or are in any single embodiment of the subject matter. Rather, language referring to the features and advantages is understood to mean that a specific feature, advantage, or characteristic described in connection with an embodiment is included in at least one embodiment of the subject matter of the present disclosure. Thus, discussion of the features and advantages, and similar language, throughout this specification may, but do not necessarily, refer to the same embodiment.

Furthermore, the described features, structures, advantages, and/or characteristics of the subject matter of the present disclosure may be combined in any suitable manner in one or more embodiments and/or implementations. In the following description, numerous specific details are provided to impart a thorough understanding of embodiments of the subject matter of the present disclosure. One skilled in the relevant art will recognize that the subject matter of the present disclosure may be practiced without one or more of the specific features, details, components, materials, and/or methods of a particular embodiment or implementation. In other instances, additional features and advantages may be recognized in certain embodiments and/or implementations that may not be present in all embodiments or implementations. Further, in some instances, well-known structures, materials, or operations are not shown or described in detail to avoid obscuring aspects of the subject matter of the present disclosure. The features and advantages of the subject matter of the present disclosure will become more fully apparent from the following description and appended claims or may be learned by the practice of the subject matter as set forth hereinafter.

Similarly, reference throughout this specification to "one embodiment," "an embodiment," or similar language means that a particular feature, structure, or characteristic described in connection with the embodiment is included in at least one embodiment of the subject matter of the present disclosure. Appearances of the phrases "in one embodiment," "in an embodiment," and similar language throughout this specification may, but do not necessarily, all refer to the same embodiment. Similarly, the use of the term "implementation" means an implementation having a particular feature, structure, or characteristic described in connection with one or more embodiments of the subject matter of the present disclosure, however, absent an express correlation to indicate otherwise, an implementation may be associated with one or more embodiments.

Various embodiments of the present invention allow water samples to be quickly tested for analytes in very few steps, with little need for training and with no need for reactive or labile liquid reagents. Detection of the analytes is accomplished through chromogenic or fluorescence testing initiated by reconstitution of pre-dosed vials containing solid or freeze-dried reagents with the sample where the detected analyte is quantified through use of absorption or fluorescence chromophores generated by reaction with the analyte and as quantified by a detection instrument capable of converting detected light signals into electronic signals. In some embodiments, an analyte reacts with reagents provided in a pre-dosed vial with said pre-dosed vial determining which analyte is to be detected and quantified. Another embodiment of the invention uses the human eye versus a comparison chart to quantify the chromophore in the sample. Yet another embodiment of the present invention would utilize the photographic image of the test vial and use of a comparison to known color values to quantitate the chromophore (and thus the analyte) in the sample. Some embodiments utilize the benefits of the dried, pre-dosed vials.

FIG. 1 shows a diagram 100 illustrating the steps and processes necessary to practice an embodiment of the present invention. In step 1, a specific amount of a sample including an analyte is used to reconstitute a sample vial containing dried chemicals specific for the detection and quantitation of the analyte in question. The sample vial is mixed to completely dissolve the dried reagent in step 2. In step 3, the reconstituted vial is placed in an optical chamber 824 (see e.g., FIG. 8) of a detection device capable of determining an amount of light transmitted through, scattered, and emitted due to fluorescence. For each light source, the light is frequency modulated and passed into the sample vial. In some embodiments, detection of the transmitted light intensity is accomplished using photodetectors directly in the path of the respective light source on the other side of the sample vial. In some embodiments, detection of the scattered and fluorescent light is accomplished using a photodetector at a right angle to the sample vial. Amplification followed by analog-to-digital conversion and demodulation converts the signal detected into a digital signal, which is used to quantitate the analyte in question. The reconstitution, mixing and placement of the mixed sample is required only once per sample whereas the frequency modulation, amplification and demodulation of each transmitted light and scattered light signals are required for each light source used.

Figure 2:
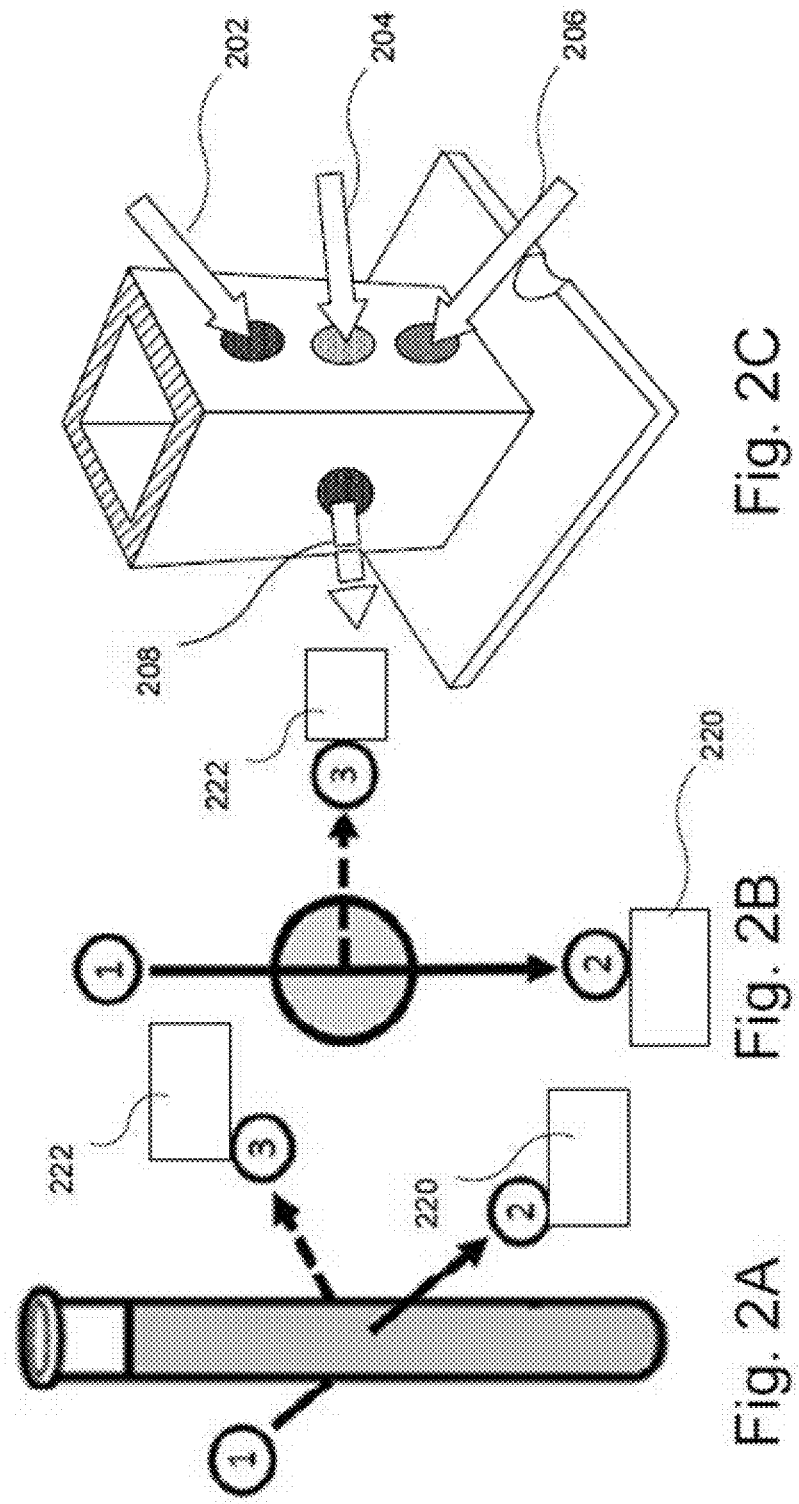
FIG. 2A is a perspective view of a vial containing a volume of water to be tested, according to one embodiment.
FIG. 2B is a cross-sectional view of the vial of FIG. 2A, according to one embodiment.
FIG. 2C is a perspective view of a spectrometer device, according to one embodiment.

FIGS. 2A and 2B further show the mechanical relationship of a light source directed into the sample (1), the transmitted light (2) and the fluoresced and scattered light (3) relative to the sample vial (both side and top views). Some embodiments teach the use of multiple light sources with various wavelengths which should be aimed at a photodetector opposite the optical chamber for the detection of transmitted light (see e.g., photodetector 220) and an additional photodetector at a right angle to the transmission photodetector for the detection of scattered and fluoresced light signals (see e.g., photodetector 222). The embodiment illustrated in FIG. 2C shows a mechanical assembly allowing multiple laser light sources 202, 204, 206 aimed at different angles so as to strike the active area of a single photodetector opposite the sources; the aperture 208 for the additional photodetector used to detect fluorescence and scattering can be seen. In an embodiment of the invention, angling all light sources to a single detector opposite allows detection of both transmission and fluorescence and scattering with only two photodetectors as long as each light source is modulated separately.

Figure 3:
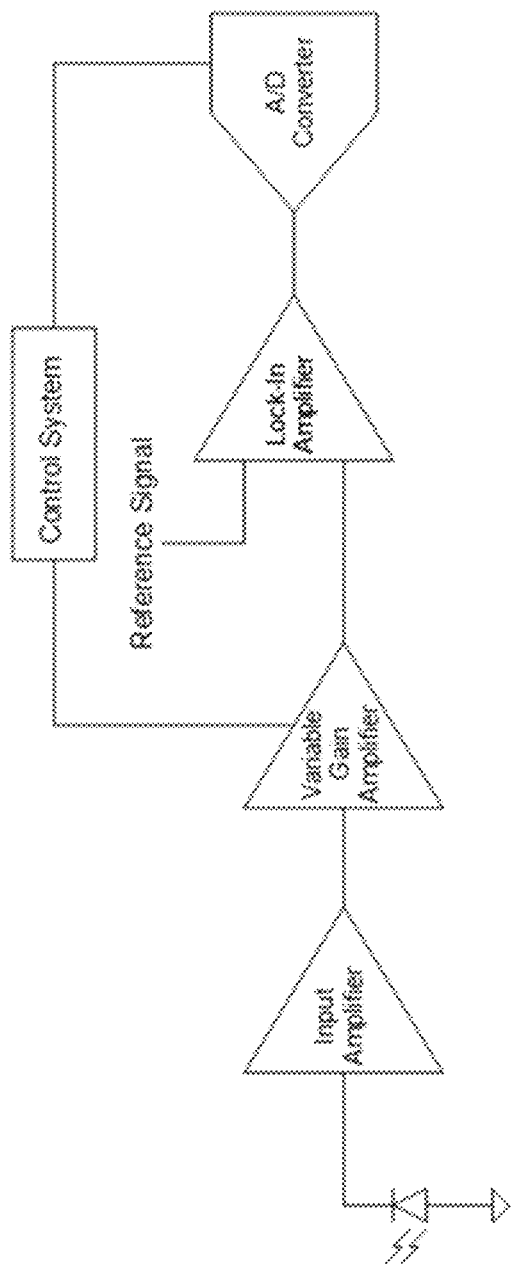
FIG. 3 is a schematic circuit diagram for operation of the spectrometer device, according to one embodiment.

FIG. 3 shows the circuit diagram of how frequency-modulated light is converted to an electrical signal by use of photosensitive detector whose signal is amplified then subsequently demodulated to produce a DC signal that is measured by an analog to digital converter. In some embodiments, demodulation is accomplished using a balanced demodulator configured as a lock-in amplifier.

Figure 4:
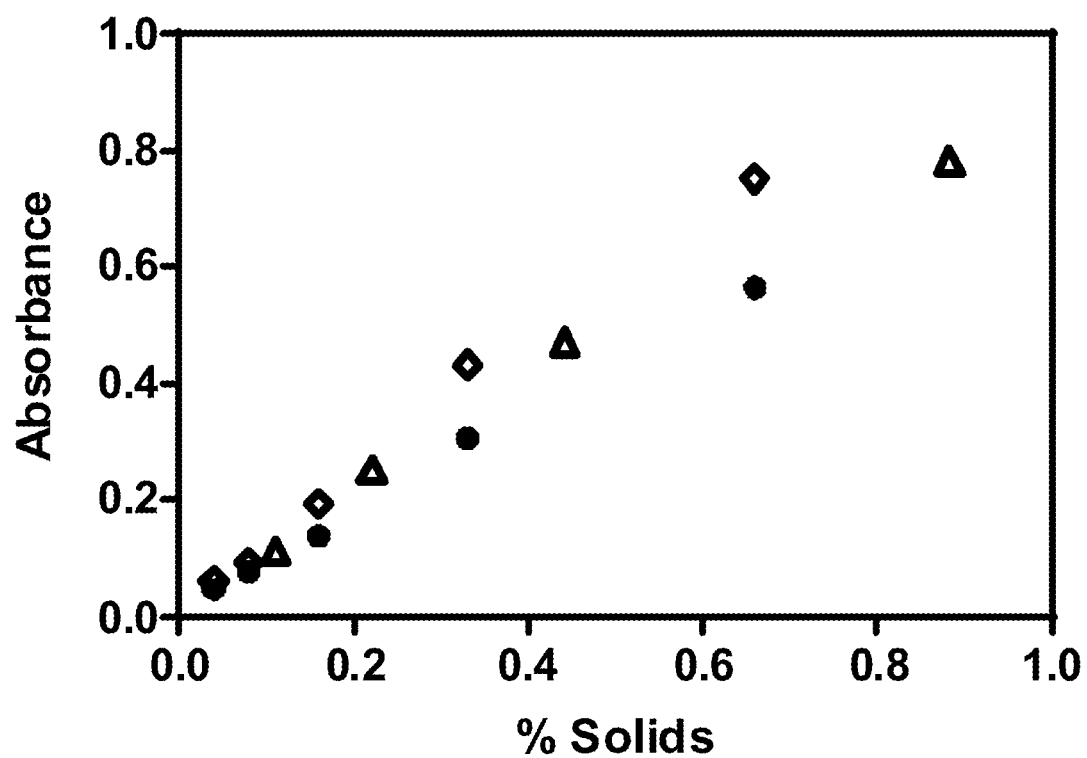
FIG. 4 is a chart showing absorbance (770 nm wavelength) as a function of solids percent in wastewater for various sizes of latex microspheres, according to one embodiment.

FIG. 4 shows the absorbance at 770 nm in water with varying amounts and sizes (● 0.202 µm, ◊ 0.548 µm, and Δ 1.053 µm) of latex microspheres. This shows that the amount of absorbance due to scattering can be predicted for a wide variety of particle sizes normally observed in hydraulic fracturing flowback wastewater.

Figure 5A:
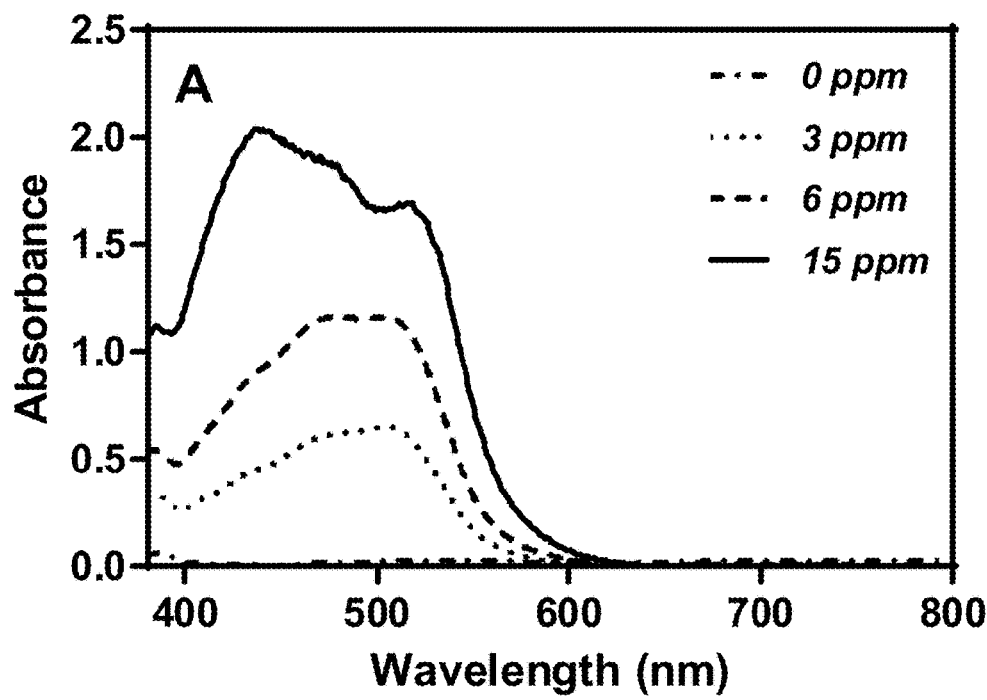
FIG. 5A is a chart showing absorbance as a function of wavelength for various concentrations of iron, according to one embodiment.
Figure 5B:
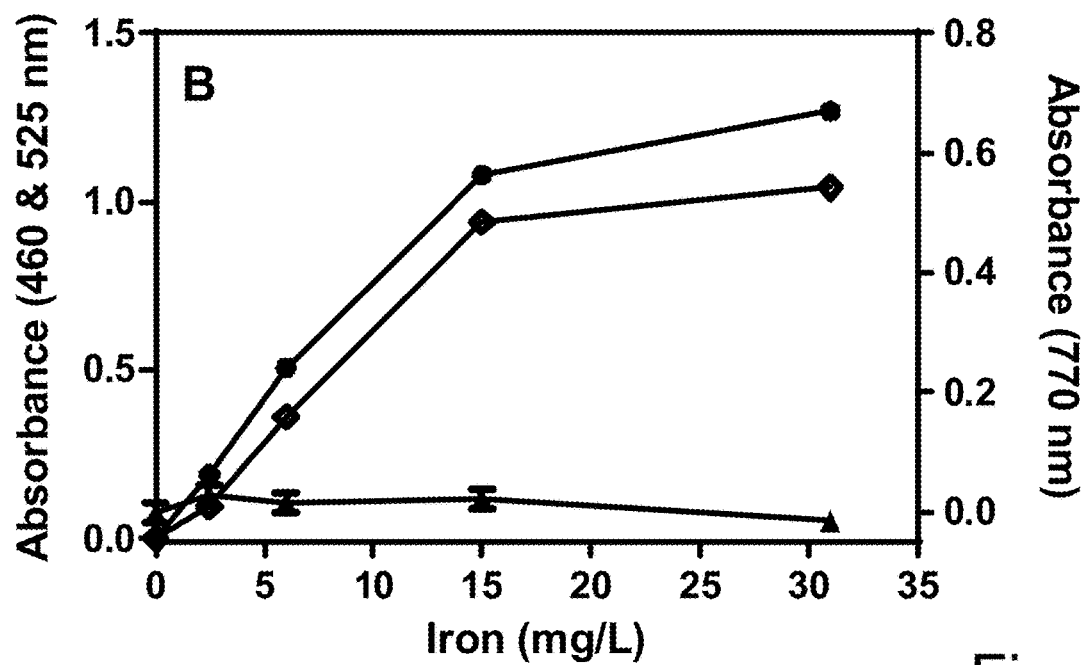
FIG. 5B is a chart showing absorbance as a function of iron concentration for various wavelengths, according to one embodiment.

FIG. 5A is a chart showing absorbance as a function of wavelength for various concentrations of iron. FIG. 5B is a chart showing absorbance as a function of iron concentration for various wavelengths.

FIGS. 5A and 5B show the absorbance spectra (A) of the 1,10-phenanthroline reaction with varying amounts of iron. (As the amount of iron present in the sample increases, so does the absorbance form the generated chromophore present.) The effect of total iron in the sample on the calculated absorbances from the 460 nm (●) and 525 nm (◊), and 770 nm (Δ) transmissions in an embodiment of the invention is shown. The calculated absorbance values at 460 and 525 nm are useful to determine how much of the chromophore is present; the calculated absorbance value at 770 nm is insensitive to the chromophore but can be used to predict the contribution at 460 and 525 nm of the calculated absorbance from scattering in the sample.

Figure 6A:
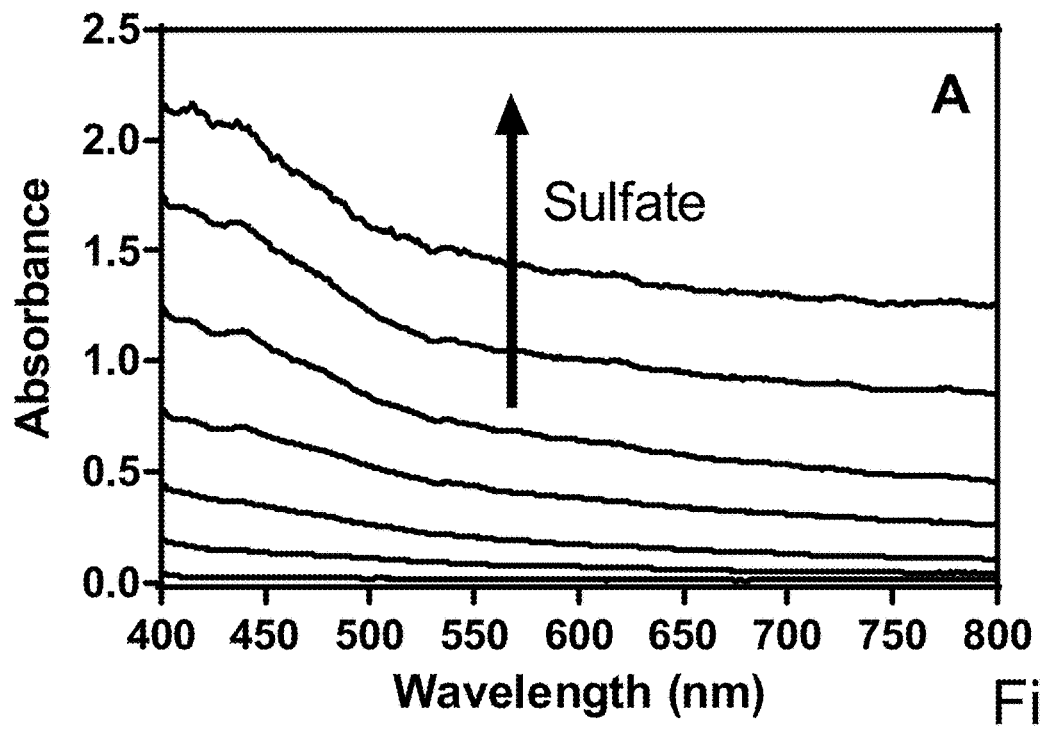
FIG. 6A is a chart showing absorbance as a function of wavelength for various amounts of sulfate, according to one embodiment.
Figure 6B:
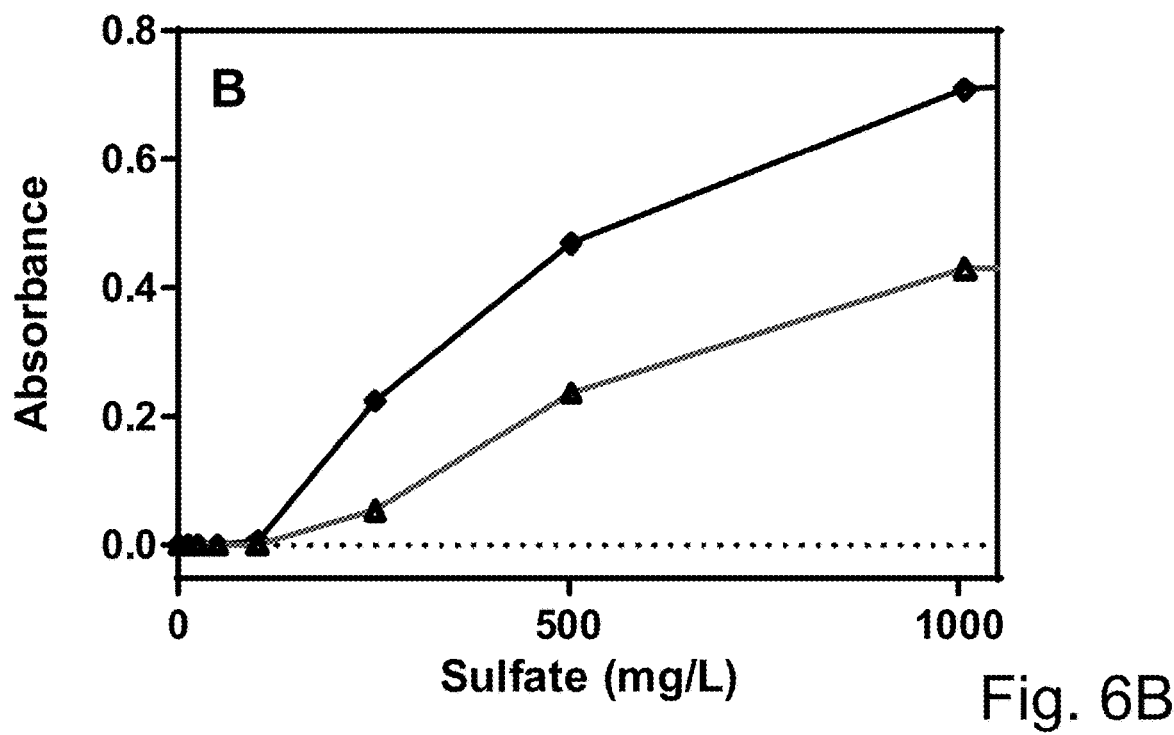
FIG. 6B is a chart showing absorbance as a function of sulfate concentration for various wavelengths, according to one embodiment.

FIG. 6A is a chart showing absorbance as a function of wavelength for various amounts of sulfate. FIG. 6B is a chart showing absorbance as a function of sulfate concentration for various wavelengths.

FIGS. 6A and 6B show the absorbance spectra (A) of the barium reaction with varying amounts of sulfate. (As the amount of sulfate present in the sample increases, so does the absorbance due to scattering from the generated solids present.) The effect of sulfate in the sample on the calculated absorbances from the 660 nm (●) and 525 nm (Δ) transmissions in an embodiment of the invention is shown.

Figure 7A:
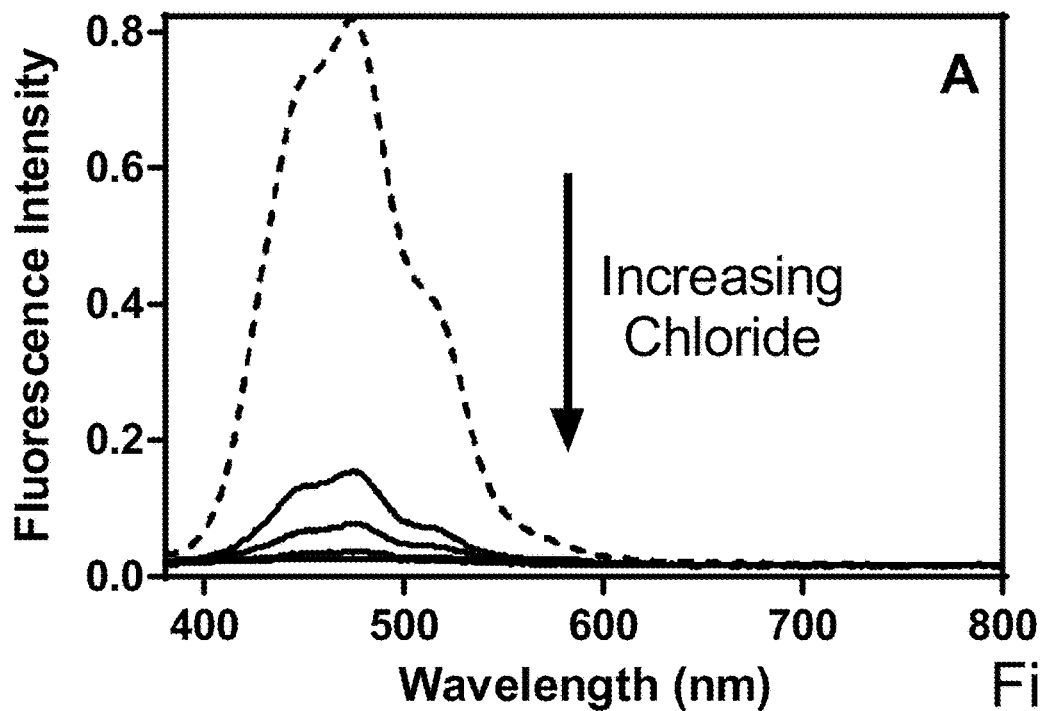
FIG. 7A is a chart showing fluorescence intensity as a function of wavelength for various amounts of chloride, according to one embodiment.
Figure 7B:
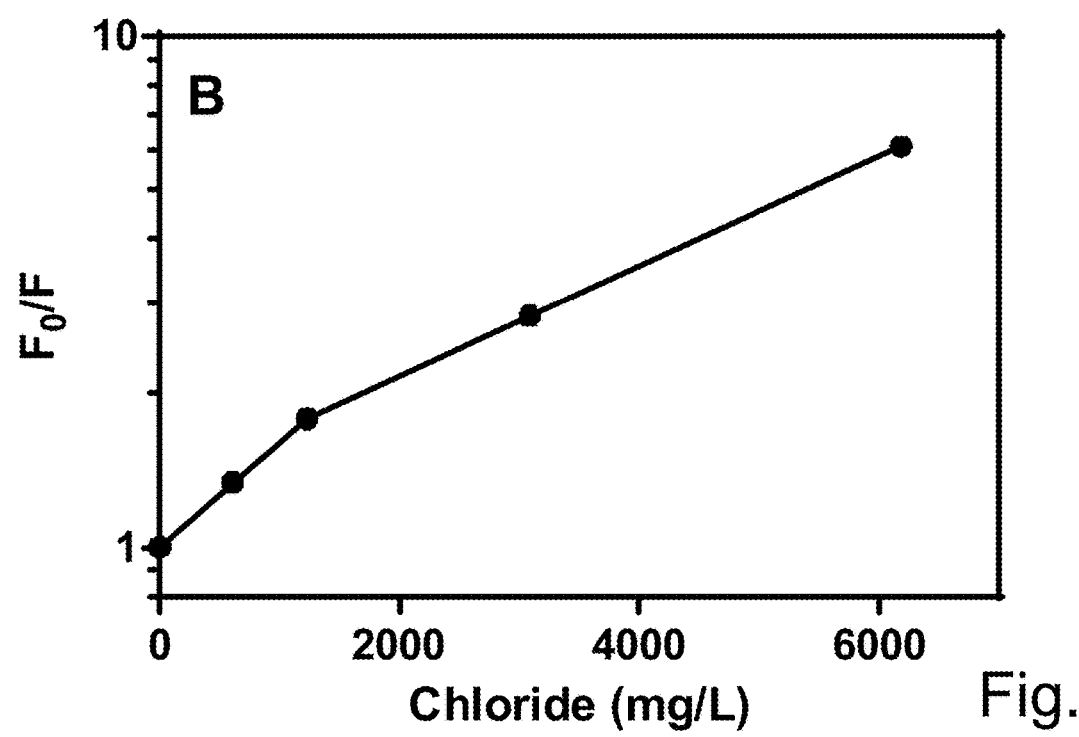
FIG. 7B is a chart showing a fluorescence ratio of pure water to water with chloride as a function of chloride concentration.

FIG. 7A is a chart showing fluorescence intensity as a function of wavelength for various amounts of chloride. FIG. 7B is a chart showing a fluorescence ratio of pure water to water with chloride as a function of chloride concentration.

FIGS. 7A and 7B show the fluorescence spectra (A) of the buffered quinine interaction with varying amounts of chloride. (As the amount of chloride present in the sample increases, the fluorescence is quenched.) B shows the effect of chloride in the sample on the calculated ratio of the fluorescence from pure water (F0) to the sample (F) upon excitation with ultraviolet light (●).

Figure 8:
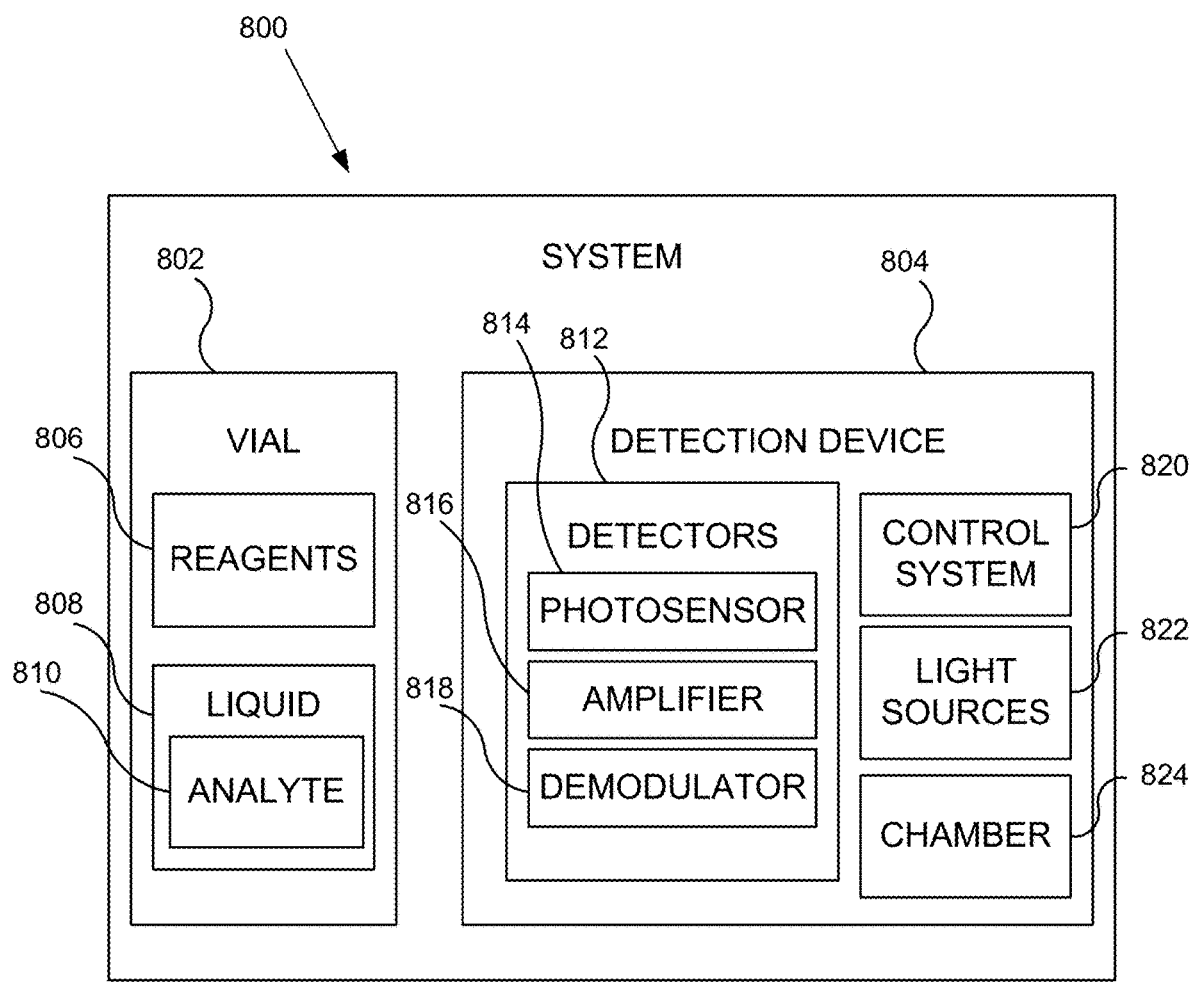
FIG. 8 is a schematic diagram of an embodiment of a system for detecting and quantifying an analyte in a liquid.

Embodiments of the present invention describe a method, a system, and an apparatus. Referring to FIG. 8, the system 800 and/or apparatus can be constructed to practice embodiments of the method, for the detection and quantitation of an analyte 810 in a solution or liquid 808 by reaction with a reagent 806 or collection of reagents 806 that will result in a change in color or fluorescence; this change in color or fluorescence can be used to subsequently determine the concentration of the analyte 810. This method may be practiced where all the reagents 806 necessary to result in detection and quantitation are pre-dosed and dried in a reaction vial 802 in a manner that will result in them being quickly dissolved when reconstituted with the sample (e.g., liquid 808). Successful production of the pre-dosed reaction vials 802 requires that the chromogenic chemistries are compatible with substances that are likely to be present in the sample and may require bulking agents, whether buffering salts, soluble starches, other organic compounds that will not interfere with the reaction chemistries, unreactive inorganic salts, or a mixture thereof. In some embodiments, if the reaction chemicals are not compatible with each other before reaction with the analyte 810, it is necessary to freeze these incompatible reagents separately in the vial before freeze-drying or be kept physically apart in the same vial then freeze-dried separately.

The quantitation of the resulting chromophores or fluorophores is accomplished using an apparatus capable of measuring the amount of transmittance through and fluorescence from the reconstituted sample (e.g., a sample liquid solution) in the vial 802. An apparatus (e.g., detection device 804) includes two or more light sources 822 (optimally practiced using LASER diodes or light-emitting diodes (LEDs) that are mechanically aimed at the active area of at least two photodetectors 812); at least one of these photodetectors 812 should be oriented to measure transmission through the sample of the various light sources and at least one of the other photodetectors 812 be mechanically oriented at an angle large enough to measure fluorescence and scattering. (The absorbance due to the sample from each light source can be calculated by comparison to sample vials reconstituted with a solution without the analyte.)

In an embodiment of the invention the light sources 822 are modulated at a fixed frequency and power levels and the subsequent transmitted, scattered and fluoresced amount of light is converted to an electrical signal by use of the photodetectors 812 whose signals are amplified and demodulated to produce a direct current (DC) signal that is measured by an analog to digital converter (ADC); demodulation of the DC signal is accomplished using a balanced demodulator configured as a lock-in amplifier. Ultimately, the concentration of the analyte in the original solution is calculated from the contribution to the detected and demodulated signals from the resulting chromophore or fluorophore from which the contribution of scattering has been subtracted. Further details of the disclosed embodiments are provided below.

The detection and quantitation of each analyte in a sample is accomplished by the reaction of the analyte in the sample with dried reagents in the sample vial that will yield a chromophore, a fluorophore or both, with the quantities of said chromophores or fluorophores being determined by the quantity of the analyte in question. The quantitation of said chromophores or fluorophores is used to quantitate the amount of analyte present in the sample.

Quantifying the absorption or fluorescence chromophores generated by reaction with the analyte can be accomplished using a detection instrument capable of converting detected light signals into electronic signals. Said detection instrument is capable of detecting both absorbance (via measurement of transmission and the subsequent conversion of this measurement to absorption by comparison to the expected result of a pure water sample tested with the testing vials) and fluorescence. Such an instrument is constructed using mechanical and optical components to deliver light to the sample vials in a reproducible manner and electronics capable of detecting light that is transmitted, scattered or due to fluorescence from the sample. These functions are accomplished through the use of three subsystems: light sources, detectors, and a control system.

In an embodiment of the invention, light is produced by solid-state light sources 822 such as light-emitting diodes or diode lasers. To reduce the effect of noise and ambient light, the light sources 822 are modulated at a fixed frequency. To compensate for changes in light source efficacy over temperature, an optical feedback system can be used to monitor the light source output and adjust the drive current as required. Light from the sources is directed through the sample to a photodetector 812 that measures transmission. A second photodetector 812, facing the sample at an angle, measures scattering and fluorescence. The detector portion of the system consists of three stages: a photosensor 814, variable gain amplifier 816, and demodulator 818. The photosensor stage converts the light to a voltage signal. This signal is then amplified in the variable gain stage. The gain of this stage is adjustable to extend the dynamic range of the system 800 and maximize the range of samples that can be measured by the system. After amplification, the signal is demodulated to produce a DC signal, which is measured by the analog to digital converters in the control system 820. Demodulation of the signal is accomplished using a balanced demodulator configured as a lock-in amplifier. This design allows for a very narrow bandwidth. By narrowing the bandwidth, the effect of thermal noise, which is proportional to the square root of the bandwidth, is significantly reduced. This also allows for greater rejection of interference from fixed frequency sources.

The use of modulated light sources also significantly reduces interference from ambient light. The system electronics are controlled by an embedded microcontroller. The system can be run in two different modes: a 'stand-alone' mode or in a 'remote' mode where the user interacts with the device through a computing device connected by an electronic interface. In 'stand-alone' mode, the control system handles user input of measurement parameters, collection of transmission, scattering, and fluorescence measurements, analysis of the collected data, and display of the results to the user. In 'remote' mode, this system handles reception of commands from the connected computing device, collection of transmission, scattering, and fluorescence measurements, and transmission of the collected data back to the connected computing device.

Though the present invention has been designed to reduce the number of steps and labware needed to accomplish chemical monitoring tasks it will be appreciated by one skilled in the art that embodiments can additionally be practiced in conjunction with an auto-feed unit. By automating the placement, movement, and positioning of pre-dosed testing vials it should be possible to remove all human steps during the monitoring process.

It will be appreciated by one skilled in the art that the use of frequency modulation in both the transmissive and fluorescence detection of transmitted and fluoresced light eliminates the background signal associated with the instrument. Using either methods from electronic circuit design or the mathematical solution to the real portion of Fourier Transform of the raw detected signal (with the constant set to zero) from frequency-modulated light used for either transmission or fluorescence excitation allows the user to eliminate the portion of any detected signal that arises from the electronics of the instrument. (For fluorescence this requires the frequency modulation to be significantly slower than the fluorescence lifetime of the excited state of the fluorescing species.) This leaves the detected signal being comprised of a reduction in transmission resulting from the absorption of chemical species in the sample resulting from the generation of chromophores in a chemical assay and from scattering by microscopic materials already present in the sample. The transmitted light can be converted into absorbance values using the equation Absorbance=$\log(To/T)$ where To is the transmission observed for pure water when used in the assay and T is the transmission obtained when using the sample. Conversion of the transmission to absorbance allows one to calculate the contribution of the signal from scattered light provided one knows or can estimate the size of the scattering particles, especially if absorbance values in the sample are collected at lower energy (higher wavelength) values. Accounting for the portions of the signal from the detection instrument and from scattering allows one who practices the present invention to use pre-determined values from the chromophore or fluorophore in the assay thus eliminating the need for a sample blank for each sample, eliminating the cost and additional sample manipulations associated therewith.

In one embodiment, it is useful to employ the detection and calculation of numerous wavelengths of light used to detect chromophores resulting from rapid chemical assays for any given analyte, said wavelengths ranging from the ultraviolet to the near-infrared. The detection of these several wavelengths has at least three main benefits: (1) it allows for the instrument to be used with a wider variety of chemical assays, each detectable through the absorption of different wavelengths of light energy, (2) the detection of near-infrared light allows the user to compensate for any scattering from minerals or microbes present from the sample, and (3) the detection of multiple wavelengths allows for the use of multivariate analysis to better determine the accurate concentration of the analyte from the assay used with the sample. Additionally, various algorithms (including neural networks and the like) can be employed to increase the accuracy of both detection and quantitation of the analytes in the chemical assays by using these multiple wavelengths.

It will also be appreciated by one skilled in the art, that various embodiments may use freeze-dried reagents for the chemical assays. Such an embodiment allows one to eschew the use of liquid reagents, which are susceptible to decomposition at elevated temperatures or freeze at depressed temperatures normally encountered in the field. The use of freeze-dried reagents allows the assays to be stored for extended periods of time and under conditions that would be detrimental to assays that utilize dissolved reagents.

The use of freeze-dried or solid reagents also allows the presence of all reagents necessary to conduct the assay to be placed in a single vial; this is especially useful if the various reagents react with each other either slowly over time or with deleterious effect without the presence of the analyte. By mixing and freeze-drying the reagents quickly or at depressed temperatures, it is sometimes possible to minimize the effect these side-reactions have on the performance of the assay. On many occasions it is preferable to freeze incompatible reagents separately to prevent their reaction either before freeze-drying or to freeze-dry them in different areas of the vial, preventing them from making contact in the liquid state and thus reacting. This practice of the present invention allows all necessary reagents to be present when the assay is reconstituted in the liquid state by the sample; this allows the number of steps required to complete the assay to be reduced to simply reconstitution of the reagents with the sample, mixing and determining the concentration using the absorbance or fluorescence detection instrument. It will additionally be appreciated by one skilled in the art that the practice of embodiments of the present invention greatly reduce the number of steps required to perform a titrimetric assay, where known quantities of a standardized solution containing a necessary reagent is added until an endpoint is reached, whereby the concentration of the analyte is calculated from the amount of titrant added but conducting the assay requires the additional steps associated with said titration.

In one embodiment, the chemical reagents used in the chromogenic or fluorescence assay is chosen to be compatible with the kind of water sample. For example, flowback and produced formation waters recovered in hydraulic fracturing operations from many geological formations are likely to be high in alkaline earth metals, which are likely to form scale precipitates if exposed to high pH conditions of certain assays. Thus it is preferable to account for deleterious reactions that might occur between chemical components in the assay and chemical species that are likely to form precipitates or contain naturally occurring chemical species that absorb or fluoresce in a region that will interfere with the chromophores or fluorophores generated in the assay. Thus, in an embodiment of the invention, the choice of the chemical species used in the assay is chosen to be compatible with what is likely to be present in the water sample.

For lower volume samples the amount of reagents required to conduct the assay is usually quite low. When small amounts of organic and inorganic materials are freeze-dried they will often become closely associated with the vial surface or crystalize and exhibit a reluctance to quickly dissolve, thus increasing the time and effort required to conduct the assay. It is therefore preferable that other materials be added to the assay mix so that when the reagents are co-dried with said materials they will both quickly dissolve and keep from either becoming too tightly associated with the vial or crystallizing. In traditional chromogenic assays, a small amount of sample is added to a larger volume of solution where the pH and conductivity are carefully controlled so that the quantity of analyte can be accurately calculated from the amount of chromophore.

In one embodiment, it is necessary to provide enough buffering agent to control the pH and conductivity of the sample; this buffering agent can often be used as the material co-dried with the reagents to ensure rapid reconstitution. It is important, however, to choose buffering agents that will be compatible with the assay reagents and the components present in the sample. Additionally, soluble cellulose fibers or salts can be used for this purpose. Soluble, high molecular mass cellulose fibers such as arabinogalactans that do not interfere with an assay are useful for this purpose as they can be added without depressing the freezing point of the mixture too much making freeze-drying difficult. Alternately, a salt such as potassium chloride (which does not alter the pH of the solution) can be used for this purpose as well as increasing the ionic strength of the final testing solution (when this is desirable). In an embodiment of the invention, the choice of bulking agent used to co-dry with the analysis chemicals is based upon the needed buffering capacity relative to the sample and the chemical compatibility of that bulking agent with the assay.

The detection of calcium in waters and wastewaters is useful for purposes of determining the potential for scale, suitability for irrigation (sodicity) and determining what kind and concentration of additives will be required for oilfield use (amongst other applications). It will be appreciated by one skilled in the art that there are numerous colorimetric and fluorescence chemistries that can be used for the detection and quantification of calcium to be practiced with the present invention, these methods chosen depending on the desired calcium concentration detection range, pH and presence of interfering ions or other chemistries.

An example of these chemical methods is the use of chlorophosphonazo or arsenazo dyes, where any calcium present in the sample reacts with the dye and produces a chromophore wherein the concentration of the calcium can be determined from the concentration of the chromophore generated. By control of the pH through the provision of enough buffering chemicals to overcome the expected buffering capacity of the sample, all alkaline earth metals are detected at neutral and higher pH values; magnesium (the second most prevalent alkaline earth metal) does not form complexes with these chromophores at lower pH values. The relative concentrations of barium, strontium, and radium are so small relative to calcium in natural samples that their respective contributions to the calcium signal are negligible. Fluorophores such as calcein and chlortetracycline can be used to detect calcium with ultraviolet excitation at pH values of approximately 8 and 7, respectively. It will be appreciated by one skilled in the art that the detection and quantitation of hardness (total alkaline earth metals measured as milligrams per liter calcium carbonate) would be accomplished by practicing the calcium detection with an appropriate chemistry at a pH where calcium, magnesium, barium, strontium, and radium are all detected.

The detection of boron in waters and wastewaters is useful for purposes of determining the potential for interference in fracturing chemical gel formation (along with suitability for waters for other applications). There are numerous colorimetric and fluorescence chemistries that can be used for the detection and quantification of boron to be practiced with the present invention, these methods chosen depending on the desired boron concentration detection range, pH and presence of interfering ions or other chemistries. An example of these chemical methods is the use of azomethine-H, ammonium chloride and ascorbic acid, where any boron present in the sample reacts with the reagents producing a chromophore wherein the concentration of the boron can be determined from the concentration of the chromophore generated. pH is controlled by the addition of enough 2-(N-morpholino) ethanesulfonic acid (and its sodium salt) to overcome the expected buffering capacity of the sample. Fluorophores such as 2,3-DNHS can be used to detect boron with ultraviolet excitation.

The detection of pH in waters and wastewaters is useful for purposes of determining the potential for interference in fracturing chemical gel formation along with suitability for waters for other industrial, discharge and agricultural applications. pH monitoring is especially difficult when the sample has extremely low conductivity or moderately high conductivity as traditional electrochemical monitoring is optimized for dilute solutions containing only inorganic salts. There are colorimetric and fluorescence chemistries that can be used for the determination of pH that can be practiced with the present invention, these methods chosen depending on the desired pH determination range, pH and presence of interfering materials or other chemistries. An example of these chemical methods is the use of neutralized universal indicator and salt (potassium chloride), where the pH is determined by multivariate analysis of the relative amounts of colors present. Potassium chloride is added to overcome any expected changes in the pKas of the indicator salts as the effects of salinity on the pKa transitions is less at higher salt concentration. Fluorescent indicators to pH, such as eosin yellowish and eosin blueish, can be utilized at low pH values.

The quantitation of alkalinity in waters and wastewaters is useful for purposes of determining the Langelier Saturation Index (useful in determining the potential for scaling or corrosion) along with suitability for waters for other industrial, discharge and agricultural applications. This is accomplished by adding a known amount of sample to a known amount of weak acid that has been buffered to a pH of 4.2; the same colorimetric or fluorimetric chemistries that can be used for the determination of pH can be used to determine the resulting pH and thus the amount of total alkalinity (hydroxide and bicarbonate) can be calculated from a calibration curve previously determined. In an embodiment of the present invention, citric acid is used because it buffers over the most useful pH range for this assay, but the choice of a weak acid and the concentration used thereof should be chosen depending on the desired total alkalinity determination range, pH and presence of interfering materials or other chemistries. An example of these chemical methods is the use of universal indicator and salt (potassium chloride), where the pH is determined by multivariate analysis of the relative amounts of colors present. Different amounts of a weak acid can be used to produce assays that have larger or smaller ranges of total alkalinity.

Chloride determination in waters and wastewaters is useful for purposes of estimating total dissolved solids as the most prevalent salt in wastewaters is sodium chloride. There are numerous colorimetric and fluorescence chemistries that can be used for the detection and quantification of chloride to be practiced with the present invention, these methods chosen depending on the desired chloride concentration detection range, pH and presence of interfering ions or other chemistries. An example of these chemical methods is the use of quinine sulfate, where any chloride present in the sample quenches the fluorescence from the quinine, wherein the concentration of the chloride (and other rare halides) can be determined from the degree of quenching compared to a solution of pure water when excited with ultraviolet light. The pH is controlled by the addition of enough sulfamic acid and sodium citrate to overcome the expected buffering capacity of the sample.

Copper determination in waters and wastewaters is useful for purposes of quantifying this micronutrient for agricultural purposes and for verifying its presence for biocidal activity. There are numerous colorimetric and fluorescence chemistries that can be used for the detection and quantification of copper to be practiced with the present invention, these methods chosen depending on the desired copper concentration detection range, pH and presence of interfering ions or other chemistries. An example of these chemical methods is the use of calcein, where any copper present in the sample quenches the fluorescence from the calcein, wherein the concentration of the copper can be determined from the degree of quenching compared to a solution of pure water when excited with ultraviolet light. The pH is controlled by the addition of enough citric acid and sodium citrate to overcome the expected buffering capacity of the sample.

The detection of hexavalent chromium in waters and wastewaters is useful for purposes of determining the suitability for discharge or effectiveness of treatment regimes. There are numerous colorimetric and fluorescence chemistries that can be used for the detection and quantification of hexavalent chromium to be practiced with the present invention, these methods chosen depending on the desired hexavalent chromium concentration detection range, pH and presence of interfering ions or other chemistries. An example of these chemical methods is the use of 1,5-diphenylcarbazide, where any hexavalent chromium present in the sample reacts with the reagents producing a chromophore wherein the concentration of said hexavalent chromium can be determined from the concentration of the chromophore generated. pH is controlled by the addition of enough buffered sulfamic acid to overcome the expected buffering capacity of the sample.

The detection of iron in waters and wastewaters is useful for purposes of determining the potential for interference in fracturing chemical gel formation, the tendency to form scale and for waters for other industrial and agricultural applications. There are numerous colorimetric and fluorescence chemistries that can be used for the detection and quantification of iron to be practiced according to various embodiments, these methods chosen depending on the desired iron concentration detection range, pH and presence of interfering ions or other chemistries. An example of these chemical methods is the use of 5-sulfosalicilic acid or 1,10-phenanthroline, where any iron present in the sample reacts with the reagents producing a chromophore wherein the concentration of the iron can be determined from the concentration of the chromophore generated. Speciation between divalent, trivalent or total iron is determined by pH, which can be controlled by the addition of enough citric acid (and its sodium salt) to overcome the expected buffering capacity of the sample.

The detection of sulfate in waters and wastewaters is useful for purposes of determining the potential for barite and other alkaline earth metal scale formation along with suitability for waters for discharge and agricultural applications. There are numerous colorimetric and fluorescence chemistries that can be used for the detection and quantification of sulfate to be practiced with the present invention, these methods chosen depending on the desired boron concentration detection range, pH and presence of interfering ions or other chemistries. An example of these chemical methods is the use of acidic barium hydroxide or barium violurate, where any sulfate present in the sample reacts with the reagents producing either a precipitate that will absorb and scatter light or a chromophore wherein the concentration of the sulfate can be determined from the concentration of the precipitate or chromophore generated. pH is controlled by the addition of enough maleic anhydride and sodium citrate to overcome the expected buffering capacity of the sample.

The detection of sulfide in waters and wastewaters is useful for purposes of determining the potential for scale formation, corrosive tendencies and the suitability for waters for discharge and other uses. There are numerous colorimetric and fluorescence chemistries that can be used for the detection and quantification of sulfide to be practiced with the present invention, these methods chosen depending on the desired sulfide concentration detection range, pH and presence of interfering ions or other chemistries. An example of these chemical methods is the use of buffered 6,6'-Dinitro-3,3'-dithiodibenzoic acid, where any sulfide present in the sample reacts with the reagents a chromophore wherein the concentration of the sulfide can be determined from the concentration of the chromophore generated. Alternately, the sulfide can be reacted with N, N-Dimethyl-p-phenylenediamine in the presence of iron chloride to produce a chromophore; buffering with sulfamic acid results in the formation of methylene blue that can be used to quantitate the sulfide.

The detection of miscible volatile or semi-volatile organic compounds (VOCs) in waters and wastewaters is useful for purposes of determining the potential for interference in fracturing chemical gel formation as well as suitability for waters for other applications or discharge. There are numerous colorimetric and fluorescence chemistries that can be used for the detection and quantification of VOCs to be practiced with the present invention, these methods chosen depending on the desired VOCs concentration detection range, pH and presence of interfering ions or other chemistries. An example of these chemical methods is the use of a buffered solvatochromatic dye like N,N-Dimethylindoaniline, where any VOC (such as acetone, alcohols and the like) present in the sample associates with the reagents producing a chromophore wherein the concentration of the VOC can be determined from the concentration of the chromophore generated. pH is controlled by the addition of enough buffering salts to overcome the expected buffering capacity of the sample.

The detection of viable microorganisms in waters and wastewaters is useful for purposes of determining the potential for microbial induced corrosion, waterflooding and other enhanced oilfield recovery operations as well as suitability for waters for other applications or discharge. There are numerous colorimetric and fluorescence chemistries that can be used for the detection and estimation of microbial concentration to be practiced with the present invention, these methods chosen depending on the desired microbial content detection range, pH and presence of interfering biocides or other chemistries. An example of these chemical methods is the use of a buffered metabolic dye precursor such as resulin, where metabolic activity (and thus viable microorganisms capable of metabolizing the dye precursor) present in the sample produces a chromophore when excited with green light wherein the concentration of the microbes can be determined from the concentration of the chromophore generated if incubated at the correct temperature and for the proper amount of time. In some embodiments, pH is controlled by the addition of enough buffering salts to overcome the expected buffering capacity of the sample and other necessary nutrients can be added to the reaction mixture. It will be appreciated by one skilled in the art that the desired level of specificity in microbial species identification may be introduced by selecting a chromogenic precursor that is metabolized only by the kingdom, genera, genus, species or subspecies of interest.

It will also be appreciated by one skilled in the art that the principles outlined in the present disclosure can be applied to fluids other than water. For example, extract solutions of solid samples which solubilize analytes into the fluid phase can be employed or other fluids like urine can be analyzed using the same methodology provided chromophores or fluorophores utilized to detect the analyte in question do not exhibit similar absorption or fluorescence to the sample. Organic liquids can also be analyzed using the same methodology: with organic solutions it is necessary that the vial be compatible with the solution, the organic liquid be somewhat transmissive to light in the energy regions utilized by the chromophores, and that the chromophores or fluorophores utilized to detect the analyte in question do not exhibit similar absorption or fluorescence to the organic liquid.

In summary, the present disclosure relates to a system, apparatus, and method for the detection and quantitation of an analyte in a solution by reaction with a reagent or reagents that result in a change in color and/or fluorescence. The concentration of the analyte can be related to the amount of change in color or fluorescence.

Regarding the reagents and the pre-dosed vial:

All the reagents required to complete the reaction may be provided as pre-dosed, freeze-dried solids that will quickly dissolve upon addition of the liquid sample.

The freeze-dried reagents may contain enough buffering agents that will exceed the buffering capacity of the sample resulting in a defined pH range for the reaction.

The freeze-dried reagents contain (if necessary) a bulking agent that will not interfere with the chemical assay to keep said reagents from crystalizing or becoming too associated with the walls of the vial in which the reaction is conducted.

The bulking agent may be an unreactive salt, buffering substances, a carbohydrate or other organic substance that doesn't interfere with the reaction, a soluble higher molecular weight starch if a freezing point depression is not desired, or a mixture of salts, buffering substances, soluble starches and other organic materials that do not interfere with the analyte detection chemistries.

The reagents, if chemically incompatible with each other before reacting with the analyte, can be frozen separately in the reaction vial before freeze-drying or kept physically apart and freeze-dried separately;

The freeze-dried reagents used in the chromogenic or fluorescence assay are chosen to be compatible with the kind of water sample;

Regarding the spectrometer device for detection and quantitation of the chromophores or fluorophores:

The light sources used for transmission and fluorescence excitation sources can be light-emitting diodes, laser diodes, or some other type of light source.

The light sources used for transmission excitation sources may include at least one that emits light at a wavelength that is sensitive to the presence of the chromophore.

The light sources used for fluorescence excitation sources may include at least one that will excite the fluorophore used for detection.

The light sources used for transmission or fluorescence excitation sources may include at least one that emits light at a wavelength useful for determining the amount of scattering from the sample.

The light sources used for transmission may be physically mounted in a manner so that their beams will pass through the sample before hitting the photodiode directly.

The light sources used for fluorescence may be mechanically mounted in a manner so that the detecting photodiode is at an angle to minimize transmissive signal.

The light sources may be modulated at a fixed frequency and at pre-defined and controlled power levels.

The transmitted, scattered and fluoresced light may be converted to an electrical signal by use of photosensitive detectors whose signals are amplified then subsequently demodulated to produce a DC signal that is measured by an analog to digital converter, wherein demodulation is accomplished using a balanced demodulator configured as a lock-in amplifier.

The concentration of the analyte in the solution is calculated from the contribution to the detected and demodulated signals from the resulting chromophore or fluorophore from which the contribution of scattering has been subtracted.

In the above description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object. Further, the terms "including," "comprising," "having," and variations thereof mean "including but not limited to" unless expressly specified otherwise. An enumerated listing of items does not imply that any or all of the items are mutually exclusive and/or mutually inclusive, unless expressly specified otherwise. The terms "a," "an," and "the" also refer to "one or more" unless expressly specified otherwise.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent to another element without being in contact with that element.

As used herein, the phrase "at least one of", when used with a list of items, means different combinations of one or more of the listed items may be used and only one of the items in the list may be needed. The item may be a particular object, thing, or category. In other words, "at least one of" means any combination of items or number of items may be used from the list, but not all of the items in the list may be required. For example, "at least one of item A, item B, and item C" may mean item A; item A and item B; item B; item A, item B, and item C; or item B and item C. In some cases, "at least one of item A, item B, and item C" may mean, for example, without limitation, two of item A, one of item B, and ten of item C; four of item B and seven of item C; or some other suitable combination.

Unless otherwise indicated, the terms "first," "second," etc. are used herein merely as labels, and are not intended to impose ordinal, positional, or hierarchical requirements on the items to which these terms refer. Moreover, reference to, e.g., a "second" item does not require or preclude the existence of, e.g., a "first" or lower-numbered item, and/or, e.g., a "third" or higher-numbered item.

The subject matter of the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. A system comprising:
a single pre-dosed vial containing all reagents of one or more pre-dosed reagents used for detecting and quantifying an analyte in a liquid, wherein:
the one or more reagents are freeze-dried solid reagents;
the single pre-dosed vial is configured to receive and hold a volume of the liquid comprising the analyte;
the one or more pre-dosed reagents are dissolvable in the volume of the liquid to form a sample liquid solution comprising chromophores or fluorophores, wherein the analyte and the one or more pre-dosed reagents react to yield the chromophores or fluorophores; and
a detection device comprising a chamber configured to retain the single pre-dosed vial, the detection device having:
a plurality of light sources that are linearly arranged such that a single imaginary line passes through each light source of the plurality of light sources; and
only two photosensitive detectors consisting of a first photosensitive detector that detects light transmitted from the plurality of light sources directly through the sample liquid solution and a second photosensitive detector that is mechanically positioned at an angle offset from direct light from the plurality of light sources to minimize transmissive signal from the any of the plurality of light sources, wherein the detection device is configured to quantify the analyte in the sample liquid solution,
wherein the one or more pre-dosed reagents and the volume of the liquid comprising the analyte remains in the single pre-dosed vial while being mixed to form the sample liquid solution and while using the only two photosensitive detectors to detect the analyte in the sample liquid solution.

2. The system of claim 1, wherein the pre-dosed reagents that are freeze-dried comprise freeze-dried solid reagents that are selected from the group of consisting of: first freeze-dried reagents that are freeze-dried separately prior to being combined in the single pre-dosed vial; second freeze-dried reagents that are freeze-dried in separate areas of the single pre-dosed vial; third freeze-dried reagents that are mixed in liquid form and freeze-dried sufficiently quickly to minimize side-reactions of the reagents with each other prior to being reconstituted by being dissolved in the volume of liquid to form the sample liquid solution; and combinations thereof.

3. The system of claim 2, wherein quantifying the analyte comprises quantifying the chromophores or fluorophores in the sample liquid solution.

4. The system of claim 3, wherein each light source is configured to emanate light towards the sample liquid solution in the single pre-dosed vial.

5. The system of claim 4, wherein the first photosensitive detector is positioned in the chamber opposite from the plurality of light sources.

6. The system of claim 5, wherein the second photosensitive detector is positioned at a right angle offset from direct light from the plurality of light sources.

7. The system of claim 6, wherein the plurality of light sources are modulated separately at a fixed frequency to allow detection of transmission, fluorescence, and/or scattering of light caused by the analyte in the sample liquid solution using the only two detectors.

8. The system of claim 6, wherein the first photosensitive detector comprises a photosensor configured to convert a light signal from the plurality of light sources to a voltage signal, an amplifier configured to amplify the voltage signal, and a balanced demodulator configured as a lock-in amplifier to convert the voltage signal to a direct current signal.

9. The system of claim 8, wherein the detection device further comprises a control system comprising an analog to digital converter to measure the direct current signal.

10. The system of claim 6, wherein, the volume of liquid used for dissolving the pre-dosed reagents continuously remains within the single pre-dosed vial during mixing and while the first photosensitive detector detects transmission of light through the sample liquid solution.

11. The system of claim 6, wherein the volume of liquid used for dissolving the freeze-dried pre-dosed reagents continuously remains within the single pre-dosed vial during mixing and while the second photosensitive detector detects fluorescence and/or scattering of light from the sample liquid solution.

12. The system of claim 3, wherein the detection device is further configured to detect light signals that pass through, scattered by, and/or emitted from the sample liquid solution and convert the detected light signals into digital signals to quantify the chromophores or fluorophores in the sample liquid solution.

13. A detection device comprising:
a chamber configured to receive and retain a single pre-dosed vial containing all reagents of one or more pre-dosed reagents used for detecting and quantifying an analyte in a liquid, wherein the reagents are freeze-dried and wherein the single pre-dosed vial is configured to receive and hold a volume of the liquid comprising the analyte, wherein the one or more pre-dosed reagents are dissolvable in the volume of the liquid to form a sample liquid solution comprising chromophores or fluorophores, wherein the analyte and the one or more pre-dosed reagents continuously remain within the single pre-dosed vial while reacting to yield the chromophores or fluorophores and while the detection device performs detecting;
a plurality of light sources that are linearly arranged such that a single imaginary line passes through each light source of the plurality of light sources, each light source configured to emanate light towards the sample liquid solution in the vial; and
only two photosensitive detectors consisting of a first photosensitive detector positioned in the chamber opposite from at least one of the plurality of light sources and a second photosensitive detector positioned at an angle offset from direct light from the plurality of light sources.

14. The detection device of claim 13, wherein the first photosensitive detector comprises a photosensor configured to convert a light signal from the plurality of light sources to a voltage signal, an amplifier configured to amplify the voltage signal, and a demodulator configured to convert the voltage signal to a direct current signal.

15. A method comprising:
forming a sample liquid solution by inserting a volume of a liquid comprising an analyte into a single pre-dosed vial containing all reagents of the one or more pre-dosed reagents that are used in detecting and quantifying the analyte, wherein the pre-dosed reagents are freeze-dried and are dissolvable in the volume of the liquid to form a sample liquid solution comprising chromophores or fluorophores, wherein the analyte and the one or more pre-dosed reagents remain continuously within the single pre-dosed vial while reacting to yield the chromophores or fluorophores and while detecting the analyte; and
quantifying the analyte in the sample liquid solution by quantifying the chromophores or fluorophores in the sample liquid solution,
wherein quantifying the chromophores or fluorophores in the sample liquid solution comprises detecting, using only two detectors consisting of a first photosensitive detector and a second photosensitive detector, light transmission through the sample liquid solution using the first photosensitive detector positioned opposite a plurality of light sources that are linearly arranged such that a single imaginary line passes through each light source of the plurality of light sources and detecting light fluorescence from the sample liquid solution using the second photosensitive detector positioned offset from direct light emanation from the plurality of light sources.

16. The method of claim 15, further comprising modulating the light sources at a fixed frequency to allow detection of transmission, fluorescence, and/or scattering of light caused by the analyte in the sample liquid solution using the only two detectors.

17. The method of claim 16, further comprising converting the detected light selected from transmission, fluorescence, scattering, and combinations thereof to an electrical signal.

18. The method of claim 17, wherein converting the detected light transmission to an electrical signal comprises converting the detected light selected from transmission, fluorescence, scattering, and combinations thereof, to a voltage signal, amplifying the voltage signal, and converting the amplified voltage signal to a direct current signal.

19. The method of claim 15, wherein quantifying the analyte in the sample liquid solution comprises detecting absorbance in the sample liquid solution.

* * * * *